(12) United States Patent  
Kotooka (10) Patent No.: US 8,000,437 B2  
(45) Date of Patent: *Aug. 16, 2011

(54) PHOTODETECTION UNIT, PHOTODETECTOR, AND X-RAY COMPUTED TOMOGRAPHY APPARATUS

(75) Inventor: Yoshihisa Kotooka, Hamamatsu (JP)

(73) Assignee: Hamamatsu Photonics K.K., Hamamatsu-shi, Shizuoka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 12/821,263

(22) Filed: Jun. 23, 2010

(65) Prior Publication Data

US 2010/0260314 A1     Oct. 14, 2010

Related U.S. Application Data

(63) Continuation of application No. 11/918,895, filed as application No. PCT/JP2006/308425 on Apr. 21, 2006, now Pat. No. 7,783,000.

(30) Foreign Application Priority Data

Apr. 22, 2005   (JP) ................................ P2005-125408

(51) Int. Cl.  
*H05G 1/64* (2006.01)  
*A61B 6/03* (2006.01)

(52) U.S. Cl. ................ 378/19; 378/98.8; 250/370.09

(58) Field of Classification Search .............. 378/19, 378/98.8; 250/370.09  
See application file for complete search history.

(56) References Cited

U.S. PATENT DOCUMENTS

| 6,163,028 | A | 12/2000 | Orava et al. |
| 6,396,898 | B1* | 5/2002 | Saito et al. ..................... 378/19 |
| 6,426,991 | B1* | 7/2002 | Mattson et al. ................ 378/19 |
| 6,465,790 | B1* | 10/2002 | Monnet et al. .......... 250/370.09 |
| 6,510,195 | B1 | 1/2003 | Chappo et al. |
| 6,522,715 | B2 | 2/2003 | Hoffman et al. |
| 6,587,538 | B2 | 7/2003 | Igarashi et al. |
| 6,917,664 | B2 | 7/2005 | Chappo et al. |
| 7,189,971 | B2 | 3/2007 | Spartiotis et al. |
| 7,190,759 | B2* | 3/2007 | Ratzmann ............... 250/370.09 |
| 7,202,482 | B2 | 4/2007 | Yokoi et al. |
| 7,339,176 | B2 | 3/2008 | El-Hanany et al. |
| 7,560,702 | B2 | 7/2009 | Meirav et al. |
| 7,564,940 | B2 | 7/2009 | Mattson et al. |
| 2002/0064252 | A1 | 5/2002 | Igarashi et al. |

FOREIGN PATENT DOCUMENTS

| CN | 1194725 | 9/1998 |
| JP | 51-9257 | 7/1974 |
| JP | 04-147700 | 5/1992 |
| JP | 7-29856 | 6/1995 |

(Continued)

*Primary Examiner* — Allen C. Ho  
(74) *Attorney, Agent, or Firm* — Drinker Biddle & Reath LLP (57) ABSTRACT

A photodetecting unit having a favorable attaching operability is provided.

In a photodetecting unit 1, two structures for attachment 30 are fixed to the rear face of a supporting substrate 20 formed by a sintered body of a ceramic. In the process of manufacturing the photodetecting unit 1, a laminate of green sheets is fired, so as to form a sintered body of a ceramic, and then each structure for attachment 30 is bonded to the rear face of the supporting substrate 20. This allows the structures for attachment 30 to be arranged accurately on the rear face of the supporting substrate 20, thereby ameliorating the attaching operability of the photodetecting unit 1.

29 Claims, 10 Drawing Sheets

FOREIGN PATENT DOCUMENTS

| | | |
|---|---|---|
| JP | 08-084217 | 3/1996 |
| JP | 10-107240 | 4/1998 |
| JP | 11-40700 | 2/1999 |
| JP | 2000-504410 | 4/2000 |
| JP | 2001-507862 | 6/2001 |
| JP | 2001-242253 | 9/2001 |
| JP | 2002-162472 | 6/2002 |
| JP | 2003-229629 | 8/2003 |
| JP | 2003-304027 | 10/2003 |
| JP | 2004-530505 | 10/2004 |
| JP | 2005-283441 | 10/2005 |
| WO | WO 03/002000 | 1/2003 |
| WO | WO 03/081282 | 10/2003 |

* cited by examiner

CHANNEL DIRECTION

SLICE DIRECTION

PHOTODETECTION UNIT, PHOTODETECTOR, AND X-RAY COMPUTED TOMOGRAPHY APPARATUS

This is a continuation application of copending application Ser. No. 11/918,895, which issued as U.S. Pat. No. 7,783,000, having a §371 date of May 14, 2008, which is a national stage filing based on PCT International Application No. PCT/W2006/308425, filed on Apr. 21, 2006. The copending application Ser. No. 11/918,895 is incorporated by reference herein in its entirety.

TECHNICAL FIELD

The present invention relates to a photodetecting unit, a photodetecting apparatus, and an x-ray tomographic apparatus which are equipped with a semiconductor substrate formed with a photodiode array.

BACKGROUND ART

An x-ray tomographic (CT: Computer Tomography) apparatus in accordance with prior art is disclosed in Patent Document 1. Taking account of defects and failures of a photodiode array and the like, the x-ray tomographic apparatus of Patent Document 1 constructs a photodetecting unit by integrating a semiconductor substrate having a photodiode array formed thereon with a ceramic substrate, and makes the photodetecting unit detachable from a base for attachment of the x-ray tomographic apparatus. This allows a maintenance operator to remove a failed photodetecting unit from the base for attachment and replace it with a new photodetecting unit.

In Patent Document 1, a semiconductor substrate smaller than the ceramic substrate is joined to the center of the front face of the ceramic substrate, while through holes penetrating through the ceramic substrate from the front face to the rear face are formed on both sides of the semiconductor substrate. The maintenance operator can attach the photodetecting unit to the base for attachment by inserting bolts through the through holes and fastening the bolts into screw holes formed in the base for attachment. In reverse, loosening the bolts fastened to the base for attachment can remove the photodetecting unit from the base for attachment.

Patent Document 1: Japanese Patent Application Laid-Open No. 2002-162472

DISCLOSURE OF THE INVENTION

Problem to be Solved by the Invention

However, there is the following problem in attaching the photodetecting unit to the base for attachment in the x-ray tomographic apparatus of Patent Document 1.

In general, for forming a through hole in a ceramic substrate, a plurality of green sheets each provided with a through hole at the same position are laminated and then are fired. However, the laminate of green sheets shrink when fired, so that the position of the through hole in the ceramic substrate and the position of a screw hole in the base for attachment may deviate from each other, whereby a bolt may fail to be fastened and fixed into the screw hole.

Therefore, for reliably making it possible to fasten and fix the bolt into the screw hole, it is necessary for the through hole to increase its diameter or have an elongated form. Thus expanding the through hole is preferred from the fact that it can cope with the case where the position of the through hole in the ceramic substrate and the position of the screw hole deviate from each other, but makes it difficult for the maintenance operator to place the photodetecting unit at a desirable position when attaching the photodetecting unit to the base for attachment, which worsens the operability in attaching the photodetecting unit.

Though the foregoing explanation relates to the problem in the case of attaching the photodetecting unit to the base for attachment of the x-ray tomographic apparatus as an example, this problem occurs when attaching the photodetecting unit to bases for attachment not only in the x-ray tomographic apparatus but also in apparatus for other purposes and photodetecting apparatus which simply detect light.

In view of the problem mentioned above, it is an object of the present invention to provide a photodetecting unit having a favorable attaching operability, and another object to provide a photodetecting apparatus and an x-ray tomographic apparatus which are equipped with such a photodetecting unit.

Means for Solving Problem

For achieving the objects mentioned above, the photodetecting unit in accordance with the present invention comprises a semiconductor substrate formed with a photodiode array constructed by arranging a plurality of photodiodes; a supporting substrate, formed by a sintered body of a ceramic, having a front face arranged with the semiconductor substrate; and a structure for attachment fixed to a rear face of the supporting substrate.

This configuration fixes the structure for attachment to the rear face of the supporting substrate, thereby making it possible to secure the structure for attachment to the supporting substrate after firing the supporting substrate, and thus allowing the structure for attachment to be accurately arranged on the rear face of the supporting substrate. Therefore, when attaching the photodetecting unit to a base for attachment, the photodetecting unit is easily placed at a desirable position, whereby the attaching operability of the photodetecting unit can be made favorable.

Also, this configuration secures the photodetecting unit through the structure for attachment fixed to the rear face of the supporting substrate, which makes it unnecessary to provide the supporting substrate with through holes as in the prior art. This can eliminate dead areas caused by through holes in the supporting substrate, whereby the semiconductor substrate can be arranged on the whole front face of the supporting substrate. Therefore, other photodetecting units, other electronic components, and the like can be arranged at positions neighboring the semiconductor substrates, so as to raise the packaging density of these components.

Preferably, in the above-mentioned photodetecting unit, at least two structures for attachment are fixed to the rear face of the supporting substrate. This configuration attaches the photodetecting unit to the base for attachment through at least two structures for attachment fixed to the rear face of the supporting substrate, and thus can stabilize the posture of the photodetecting unit after attaching it.

Preferably, in the above-mentioned photodetecting unit, the structure for attachment is formed such as to engage in a screw thread with a bolt. This configuration can favorably secure the photodetecting unit to the base for attachment by engaging the structure for attachment in a screw thread with the bolt. For example, the photodetecting unit is arranged on the base for attachment formed with a through hole, and the bolt is inserted through the through hole and then engaged in a screw thread with the structure for attachment of the photodetecting unit, whereby the photodetecting unit can be secured to the base for attachment.

Preferably, in the above-mentioned photodetecting unit, the structure for attachment is formed such that a bolt penetrates therethrough and engages in a screw thread therewith in the penetrated part. This configuration can favorably secure the photodetecting unit to the base for attachment by threadably engaging the base for attachment with the bolt in the penetrated part. For example, two structures for attachment are fixedly provided on the rear face of the supporting substrate, the base for attachment is arranged between the two structures for attachment, and bolts engaged in a screw thread with the structures for attachment are fastened, so that the base for attachment is held between the bolts, whereby the photodetecting unit can be secured to the base for attachment.

Preferably, in the above-mentioned photodetecting unit, the structure for attachment is formed such as to engage in a screw thread with a nut. This configuration can favorably secure the photodetecting unit to the base for attachment by engaging the photodetecting unit to the base for attachment in a screw thread. For example, the structure for attachment is inserted through a through hole formed in the base for attachment, and then the nut is engaged in a screw thread with the structure for attachment, whereby the photodetecting unit can be secured to the base for attachment.

Preferably, in the above-mentioned photodetecting unit, the structure for attachment is formed such that a mating member mates therewith. This configuration can favorably secure the photodetecting unit to the base for attachment by mating the mating member with the structure for attachment. For example, the mating member fixed to the base for attachment is mated with the structure for attachment, whereby the photodetecting unit can be secured to the base for attachment.

Preferably, in the above-mentioned photodetecting unit, the structure for attachment is constituted by an alloy of iron, nickel, and cobalt, and is bonded by silver brazing to a tungsten area formed on the rear face of the supporting substrate. In general, it is difficult for metal components to be bonded to a supporting substrate made of a ceramic. By contrast, the above-mentioned configuration can bond the structure for attachment to the supporting substrate made of a ceramic, while ensuring bond strength.

For achieving the above-mentioned object, the photodetecting apparatus in accordance with the present invention comprises one of the above-mentioned photodetecting units, and an base for attachment having the photodetecting unit attached thereto through a structure for attachment. This configuration can improve the attaching operability when attaching the photodetecting unit to the base for attachment. Also, the semiconductor substrate can be arranged on the whole front face of the supporting substrate.

Preferably, in the above-mentioned photodetecting apparatus, a plurality of photodetecting units are attached to the base for attachment. This configuration allows a plurality of photodetecting units to be arranged adjacent to each other.

For achieving the above-mentioned object, the x-ray tomographic apparatus in accordance with the present invention comprises an x-ray generating apparatus for generating an x-ray toward a sample, and a photodetecting apparatus for detecting light produced when the x-ray transmitted through the sample is incident on a scintillator; wherein the photodetecting apparatus has one of the above-mentioned photodetecting units and a base for attachment having the photodetecting unit attached thereto through a structure for attachment. This configuration can improve the attaching operability when attaching the photodetecting unit to the base for attachment. Also, the semiconductor substrate can be arranged on the whole front face of the supporting substrate.

Preferably, in the above-mentioned x-ray tomographic apparatus, a plurality of photodetecting units are arranged two-dimensionally in channel and slice directions, and the semiconductor substrate is arranged on the whole front face of the supporting substrate in each of the photodetecting units. This configuration allows a plurality of semiconductor substrates to be arranged two-dimensionally in the channel and slice directions without a gap, so as to make it possible to multislice an x-ray tomographic image, grasp temporal changes within the sample by conducting x-ray tomographic imaging within the sample for every short time, and so forth.

EFFECT OF THE INVENTION

The present invention can provide a photodetecting unit having a favorable attaching operability.

EXPLANATIONS OF NUMERALS AND LETTERS 1 to 5 . . . photodetecting unit; 7 . . . x-ray generating apparatus; 8 . . . sample, 9 . . . x-ray tomographic apparatus; 10 . . . semiconductor substrate; 12 . . . scintillator; 20 . . . supporting substrate; 21 . . . tungsten pattern; 24 . . . silver brazing; 25 . . . conductor pattern; 30, 70, 80, 90 . . . structure for attachment; 32 . . . fixing bolt; 40 . . . connector; 50 . . . processing board; 52 . . . adaptor; 60, 74, 84, 94 . . . base for attachment; 72 . . . bolt; 82 . . . nut; 92 . . . mating member; PD . . . photodiode

BEST MODES FOR CARRYING OUT THE INVENTION

In the following, a preferred embodiment of the photodetecting unit 1 in accordance with the present invention will be explained with reference to the drawings. The photodetecting unit 1 in accordance with the following embodiment is attached to the inside of the x-ray tomographic apparatus and constitutes a part of a photodetecting apparatus.

Figure 1:
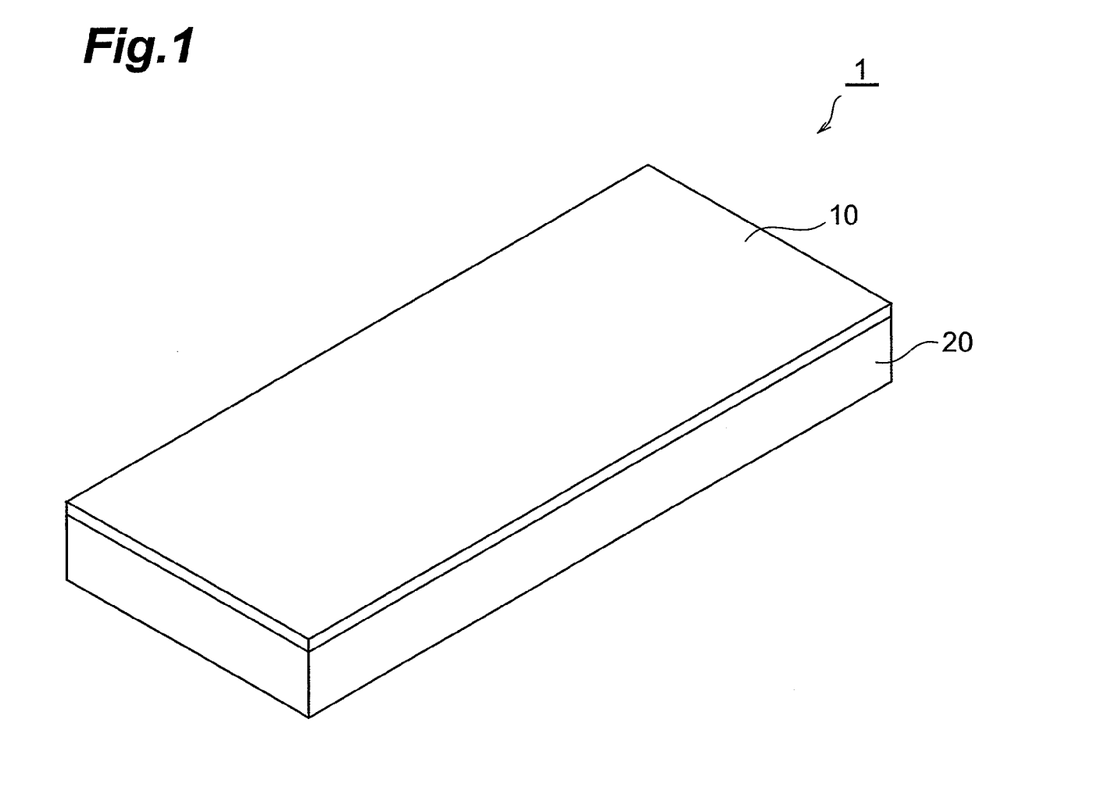
FIG. 1 A perspective view of the photodetecting unit in accordance with an embodiment of the present invention as seen from the front side.

FIG. 1 shows a perspective view of the photodetecting unit 1 as seen from the front side. The photodetecting unit 1 comprises a semiconductor substrate 10 formed with a photodiode array, and a supporting substrate 20 which is made of a ceramic and supports the semiconductor substrate 10. The semiconductor substrate 10 has a substantially rectangular board surface, on which a number of photodiodes are two-dimensionally arranged, so as to form a photodiode array. The supporting substrate 20 is a member formed by laminating a plurality of green sheets containing a ceramic and then firing them, and has a substantially rectangular board surface as with the semiconductor substrate 10. The semiconductor substrate 10 is arranged on the front face of the supporting substrate 20 such that their ends align with each other. Here, the rear face of the semiconductor substrate 10 and the front face of the supporting substrate 20 are joined together, so that the semiconductor substrate 10 and supporting substrate 20 are integrated.

Figure 2:
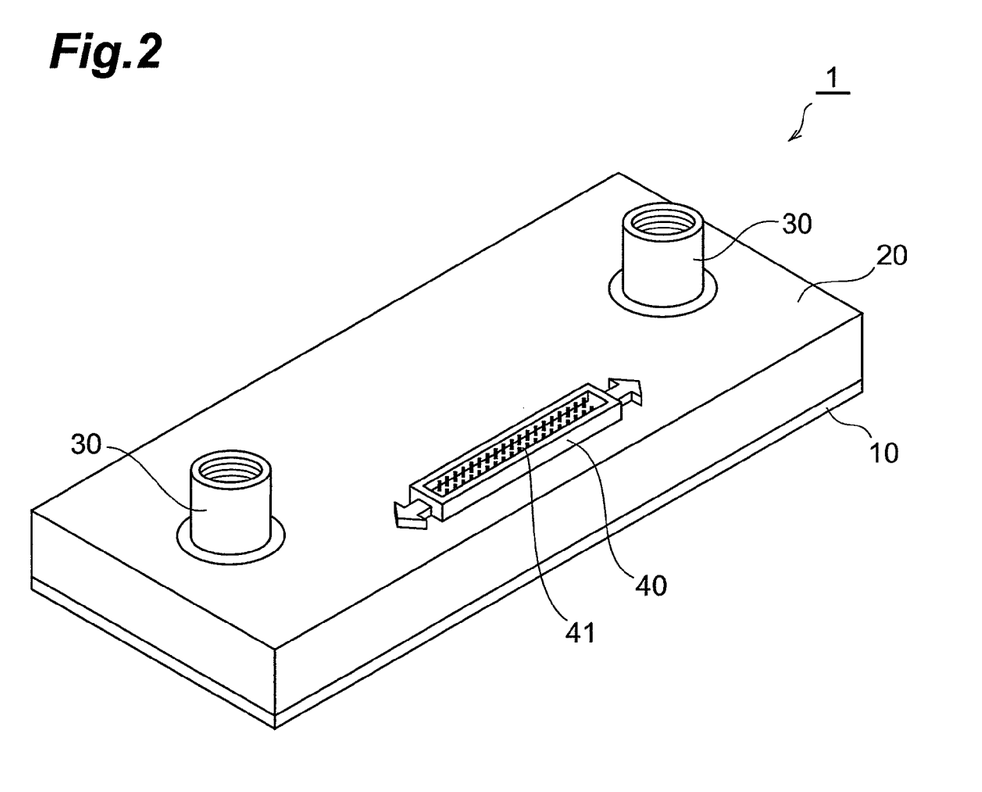
FIG. 2 A perspective view of the photodetecting unit in accordance with the embodiment of the present invention as seen from the rear side.

FIG. 2 shows a perspective view of the photodetecting unit 1 as seen from the rear side. The rear face of the supporting substrate 20 is provided with two structures for attachment 30 for securing the photodetecting unit 1 to a base for attachment, and a connector 40 for outputting detected value, photocurrents of the photodiodes to the outside. The two structures for attachment 30 are fixed to the rear face of the supporting substrate 20 at near both longitudinal ends thereof. Each structure for attachment 30 is a cylindrical member formed with a screw hole, and has one end face bonded to the supporting substrate 20. The connector 40 is provided with a plurality of pins 41 for transmitting signals.

This embodiment is configured such as to fix the structures for attachment 30 to the rear face of the supporting substrate 20 as mentioned above, and thus makes it possible to secure the structures for attachment 30 to the supporting substrate 20 after firing the supporting substrate 20 as will later be explained in detail, thereby realizing an accurate arrangement of the structures for attachment 30 on the rear face of the supporting substrate 20. This makes it easier to place the photodetecting unit 1 at a desirable position when attaching the photodetecting unit 1 to the base for attachment, thereby improving the attaching operability of the photodetecting unit 1.

Figure 3:
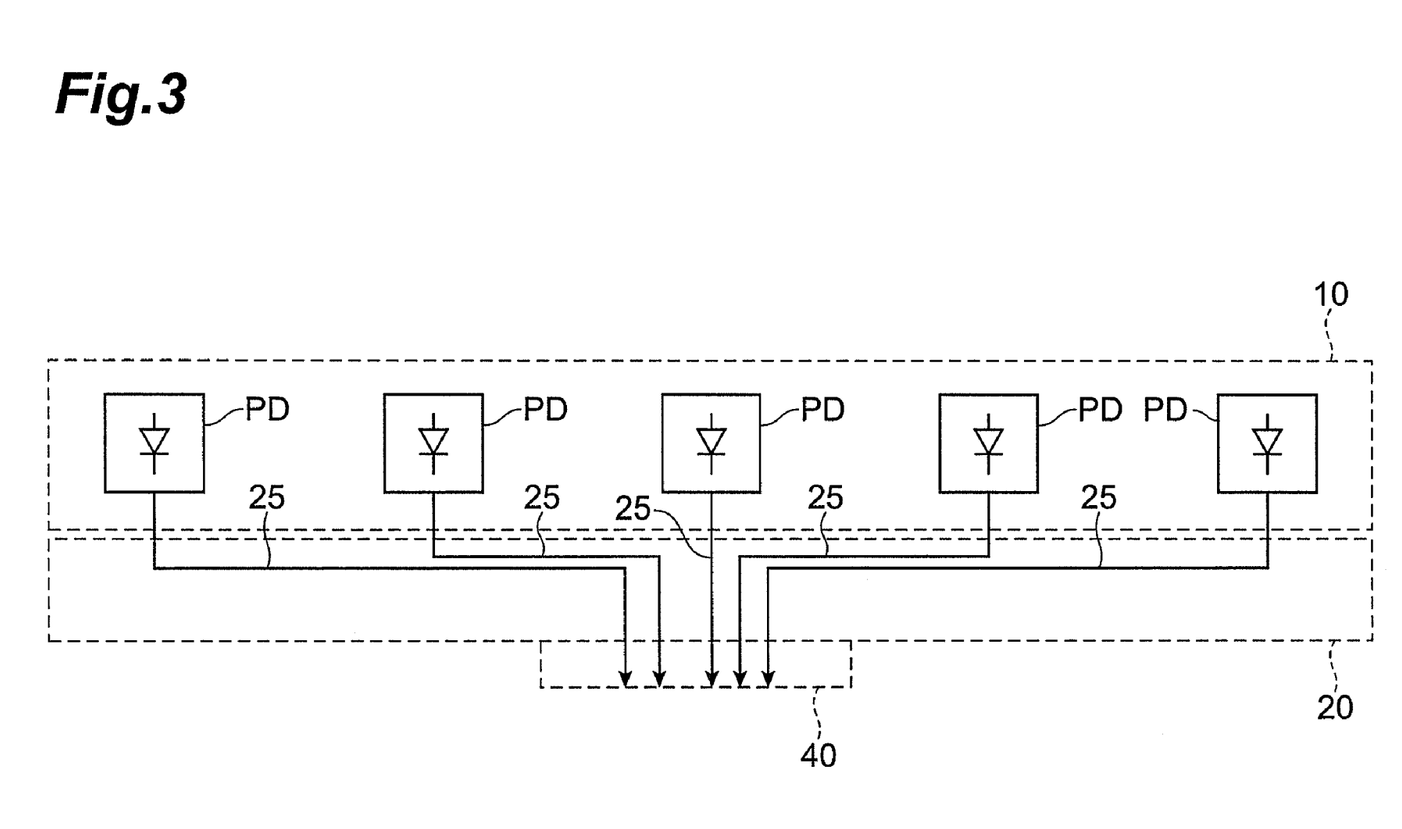
FIG. 3 A circuit diagram showing the circuit configuration within the photodetecting unit.

With reference to FIG. 3, the circuit configuration of the above-mentioned photodetecting unit 1 will now be explained. The respective photodetecting areas of the photodiodes PD are formed on the rear side of the semiconductor substrate 10, thus forming a so-called back-illuminated photodiode array. On the rear face of the semiconductor substrate 10, the photodiodes PD are connected through bumps to land electrodes formed on the front face of the supporting substrate 20, respectively. A plurality of conductor patterns 25 are provided within the supporting substrate 20, so as to connect the land electrodes on the front face of the supporting substrate 20 to their corresponding pins 41 of the connector 40. The photodiodes PD are thus connected to the pins 41, whereby the detected value, that is, photocurrents of the photodiodes PD are outputted through the connector 40 to the outside.

The photodiodes PD are of the back-illuminated type in this embodiment, but may also be of the front-illuminated type in which a photodetecting area is formed on the front side of the semiconductor substrate 10. In this case, it will be sufficient if a through-hole electrode penetrating through the semiconductor substrate 10 from the front face to the rear face is formed for each photodiode PD and is connected through the bump to the land electrode formed on the front face of the supporting substrate 20. The semiconductor substrate 10 and supporting substrate 20 may also be connected to each other by wire bonding.

Figure 4:
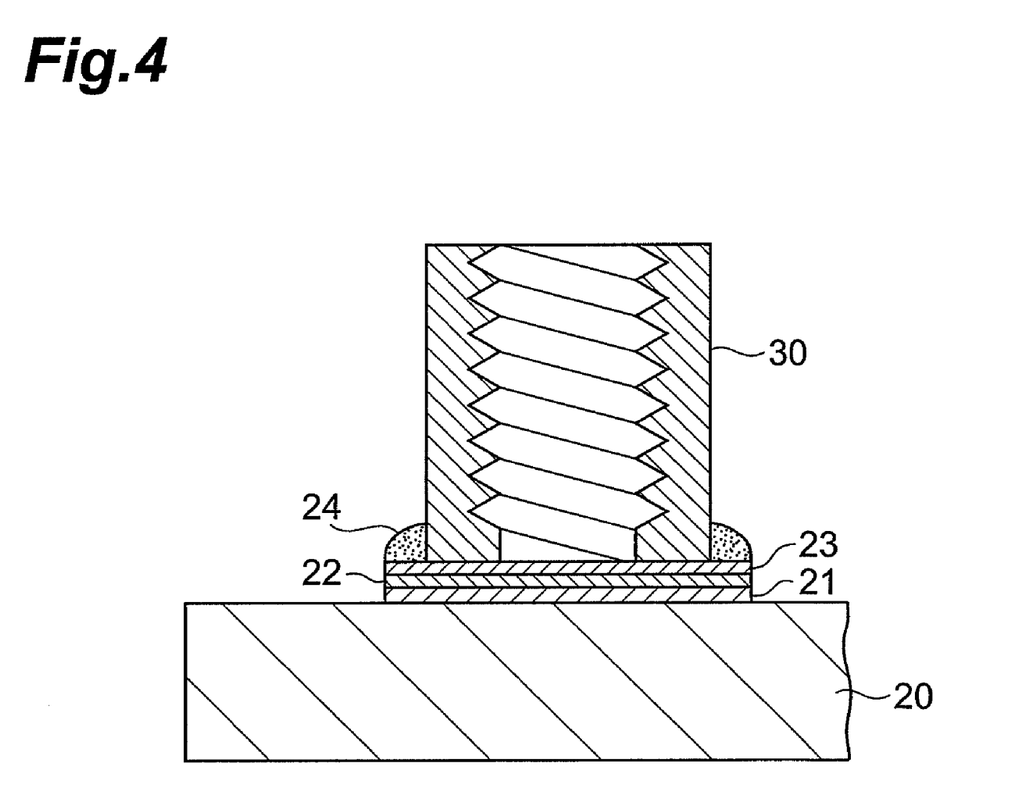
FIG. 4 A sectional view showing a configuration for attaching a structure for attachment to a supporting substrate.

With reference to FIG. 4, a method of bonding the structure for attachment 30 to the supporting substrate 20 will now be explained in detail. In the process of manufacturing the supporting substrate 20, a paste of tungsten (W) is printed on a green sheet arranged on the rear face of the supporting substrate 20, so as to form a tungsten pattern 21. After laminating a plurality of green sheets, the laminate of green sheets is fired, whereby the tungsten pattern 21 is solidified by firing. Thus formed tungsten pattern 21 is provided with a nickel (Ni) plating 22, on which a gold (Au) plating 23 is further formed. Here, it will be sufficient if the nickel plating 22 is formed by a thickness on the order of 1.27 to 8.89 μm, while the gold plating 23 is formed by a thickness of about 0.8 μm. On the other hand, the structure for attachment 30 is made of an alloy of iron, nickel, and cobalt. One end face of such an structure for attachment 30 is abutted against the tungsten pattern 21 on the rear face of the supporting substrate 20, and the abutted part is brazed with silver (Ag). As a consequence, the end face of the structure for attachment 30 and the rear face of the supporting substrate 20 are bonded to each other by silver brazing 24 while ensuring bond strength. In an x-ray tomographic apparatus, a strong centrifugal force acts on the photodetecting unit 1 in particular during when the apparatus operates. As measures against this, the above-mentioned bonding method is employed, so as to firmly secure the structure for attachment 30 and supporting substrate 20 to each other, thereby making them endurable against the centrifugal force acting on the photodetecting unit 1.

Figure 5:
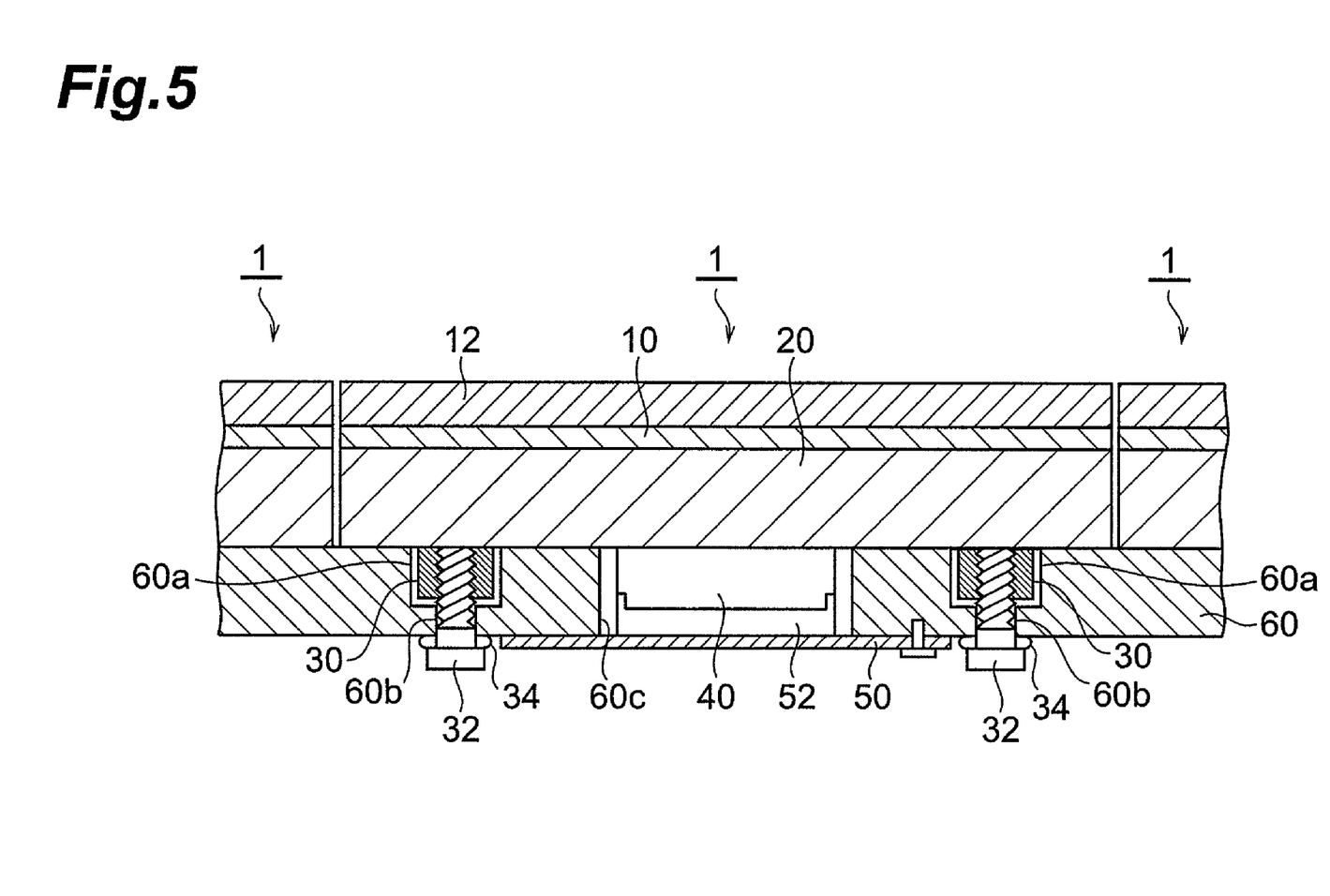
FIG. 5 A sectional view showing a configuration for attaching the photodetecting unit to a base for attachment.

With reference to FIG. 5, a configuration for attaching the photodetecting unit 1 to a body of an x-ray tomographic apparatus will now be explained. Provided within the x-ray tomographic apparatus is a gantry which rotates about a sample, while a base for attachment 60 is fixed to a part of the gantry. The base for attachment 60 is a planar member, while a plurality of photodetecting units 1 are arranged in a row on the front face of the base for attachment 60. On the front face of the base for attachment 60, escape holes 60a for keeping it from interfering with the structures for attachment 30 are formed at locations corresponding to the respective structures for attachment 30 in the photodetecting units 1. Further, an insertion hole 60b for inserting a bolt 32 is formed at the bottom part of each escape hole. The leading end of the threaded part of the fixing bolt 32 is inserted into the insertion hole 60b from the rear face of the base for attachment 60, and is fastened while engaging in a screw thread with the screw hole of the structure for attachment 30, whereby the photodetecting unit 1 is secured to the base for attachment 60. Here, as shown in the drawing, a washer 34 is held and secured between the base for attachment 60 and bolt 32, whereby the fastening can be made reliable.

At a location corresponding to the connector 40 in the photodetecting unit 1, a through hole 60c having a size larger than that of the connector 40 is formed in the base for attachment 60, while the connector 40 is arranged within the through hole 60c. On the other hand, from a processing board 50 fixed to the rear face of the base for attachment 60 by bolting, an adaptor 52 which is a part of the processing board 50 extends into the through hole 60c of the base for attachment 60, and is connected to the connector 40. Thus, the detected value, that is, photocurrents of the photodiodes are taken into the processing board 50 through the connector 40 and adaptor 52. The processing board 50 ascertains the position of a photodiode by which visible light is detected, thereby detecting a radiation.

In the above-mentioned photodetecting unit 1, a planar scintillator 12 is arranged on the front face of the semiconductor substrate 10. For example, Tl-doped CsI is used for the scintillator 12, while CsI has a structure having a forest of a number of acicular crystals (columnar crystals). The scintillator 12 converts the x-ray incident thereon from the front face thereof into visible light, and emits the resulting visible light from the rear face. This enables the photodiodes to detect the x-ray. Since the photodetecting unit 1 in accordance with this embodiment is used in an x-ray tomographic apparatus, the photodetecting unit 1 is arranged with the scintillator 12. When the photodetecting unit 1 is used in other apparatus, however, it is not necessary to arrange the scintillator 12.

Since the photodetecting unit 1 is attached to the base for attachment 60 by the above-mentioned attaching configuration, the following effects are obtained by this embodiment. Namely, the above-mentioned attaching configuration makes it possible to secure the structures for attachment 30 to the rear face of the supporting substrate 20 after firing the supporting substrate 20. When the structures for attachment 30 are thus secured after firing the supporting substrate 20, the positions where the structures for attachment 30 are attached are not affected by the thermal contraction of the supporting substrate 20, whereby the structures for attachment 30 can accurately be arranged on the rear face of the supporting substrate 20. As a consequence, the dimensional tolerance of the gap between two structures for attachment 30, which has conventionally been about ±0.5, can be reduced to about ±0.1 to ±0.2, for example. In an attaching configuration such as the one mentioned above, for preventing the structure for attachment 30 from failing to be inserted into the escape hole 60a of the base for attachment 60, it is necessary to determine the diameter of the escape hole 60a in view of the dimensional tolerance of the structure for attachment 30 in general. When the dimensional tolerance of the two structures for attachment 30 is made smaller as mentioned above, the diameter of the escape holes 60a formed in the base for attachment 60 can be decreased correspondingly thereto. When the diameter of the escape holes 60a is thus made smaller, the difference between the diameter of the structures for attachment 30 and that of the escape holes 60a decreases. Therefore, when the structure for attachment 30 is inserted into the escape hole 60a, the gap formed between the structure for attachment 30 and escape hole 60a is so small that the photodetecting unit 1 does not greatly shift its position from the base for attachment 60. This makes it easier for the operator to place the photodetecting unit 1 at a desirable position, whereby the attaching operability of the photodetecting unit 1 is made favorable.

Figure 6:
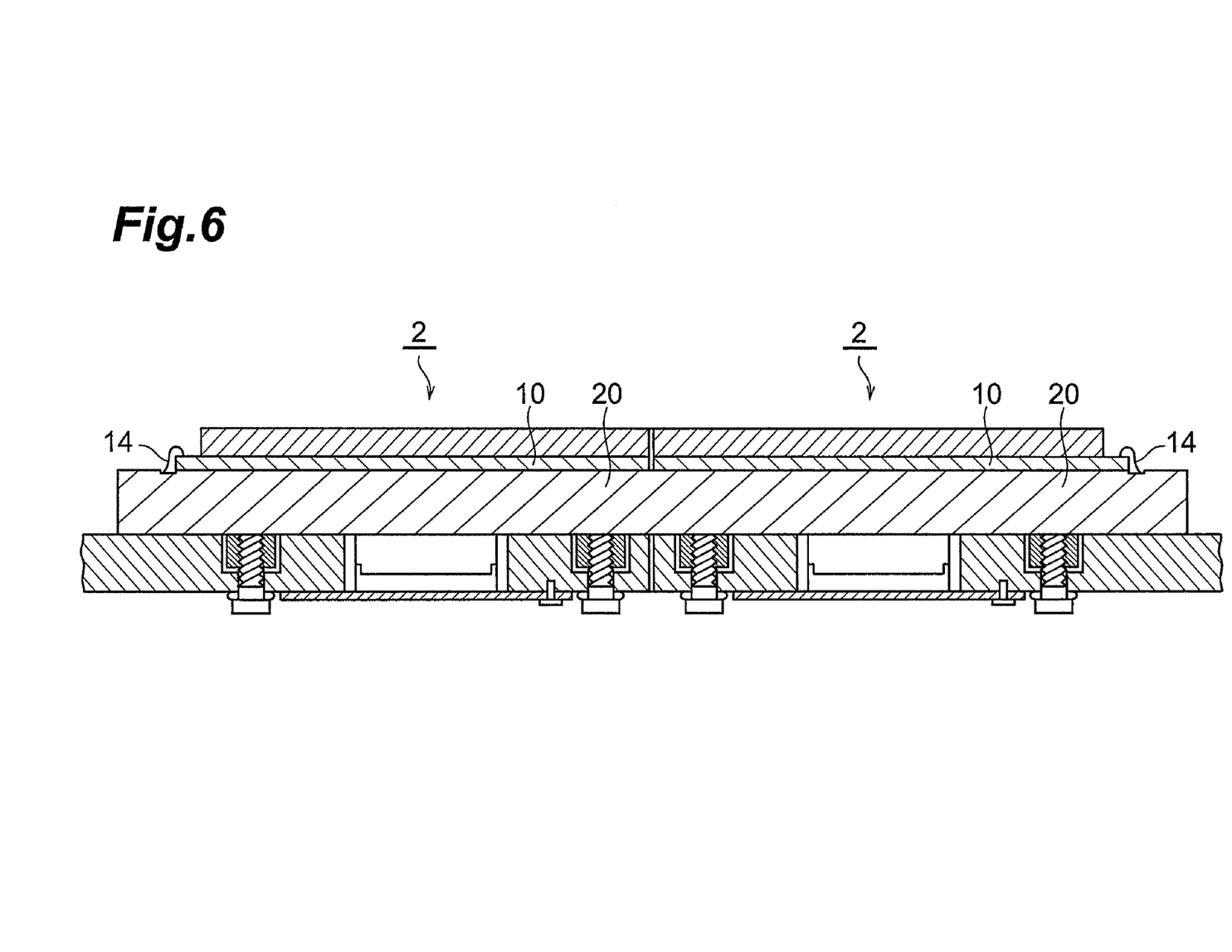
FIG. 6 A sectional view showing another example of configuration for attaching the photodetecting unit to the base for attachment in accordance with a modified example.

As mentioned above, the semiconductor substrate 10 can be arranged on the whole front face of the supporting substrate 20. Therefore, other semiconductor substrates 10 can be arranged adjacent to each semiconductor substrate 10, whereby a plurality of semiconductor substrates 10 can be arranged adjacent to each other. When the semiconductor substrate 10 is arranged on the whole front face of the supporting substrate 20, not only the other semiconductor substrates 10 but also other kinds of electronic components can be arranged adjacent thereto as mentioned above, so as to raise the packaging density of these components. When the semiconductor substrate 10 and supporting substrate 20 are connected to each other by wire bonding 14 as in the photodetecting unit 2 shown in FIG. 6, other semiconductor substrates 10 and the like can also be arranged adjacent to each semiconductor substrate 10 in end parts which are free of the wire bonding 14, whereby the packaging density of these components can be enhanced. These techniques can be utilized in a so-called chip size package (CSP).

Figure 7:
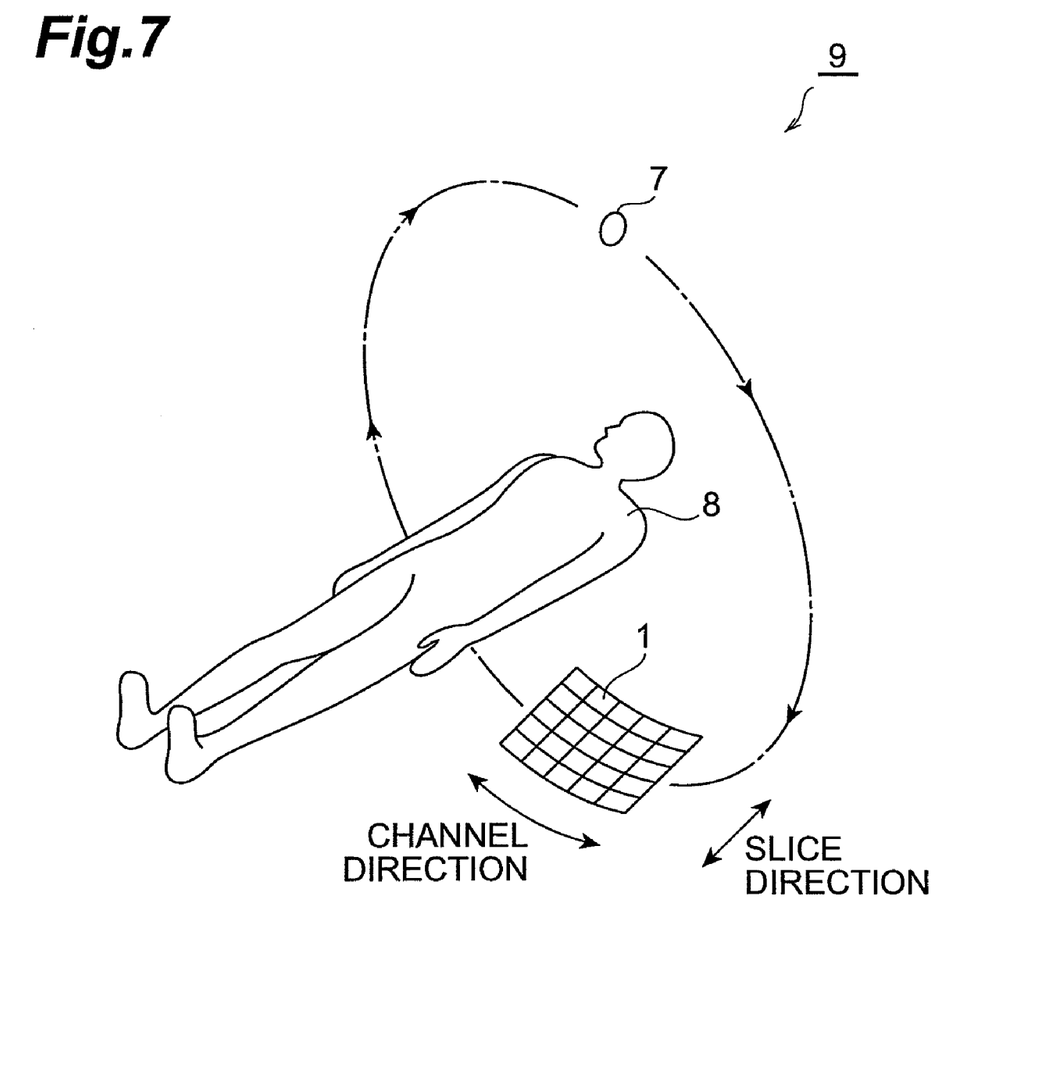
FIG. 7 A perspective view showing a schematic configuration of a tomographic apparatus.

With reference to FIG. 7, the relationship between arrangements of the x-ray generating apparatus 7 and photodetecting unit 1 within the x-ray tomographic apparatus 9 will now be explained. The gantry (not depicted) arranged within the x-ray tomographic apparatus 9 is constructed so as to rotate about a sample 8 in the arrowed direction. The x-ray generating apparatus 7 emitting an x-ray toward the sample 8 is fixed to a part of the gantry. A part of the gantry on the side opposite from the x-ray generating apparatus 7 is provided with the above-mentioned base for attachment 60, to which a plurality of photodetecting units 1 are fixed.

Here, the plurality of photodetecting units 1 are two-dimensionally arranged in channel and slice directions. Since the semiconductor substrate 10 is arranged on the whole front face of the supporting substrate 20 in each photodetecting unit 1, the plurality of semiconductor substrates 10 are densely arranged with no substantial gaps. Since the plurality of photodetecting units 1 are two-dimensionally arranged in the channel and slice directions without gaps, the gap between a photodiode formed in the periphery of each semiconductor substrate 10 and a photodiode formed in the periphery of another semiconductor substrate 10 adjacent to the former semiconductor substrate is made very small. This makes it possible to multislice an x-ray tomographic image, grasp temporal changes within the sample 8 by conducting x-ray tomographic imaging within the sample for every short time, and so forth.

Though the above-mentioned embodiment attaches the photodetecting units by fastening the bolts 32 into the screw holes in the structures for attachment 30 fixed to the rear face of the supporting substrate 20, the configuration for attaching the photodetecting units 1 is not limited thereto. For example, the configuration for attaching the photodetecting units 1 may be as in first to third modified examples which will be explained in the following.

Figure 8:
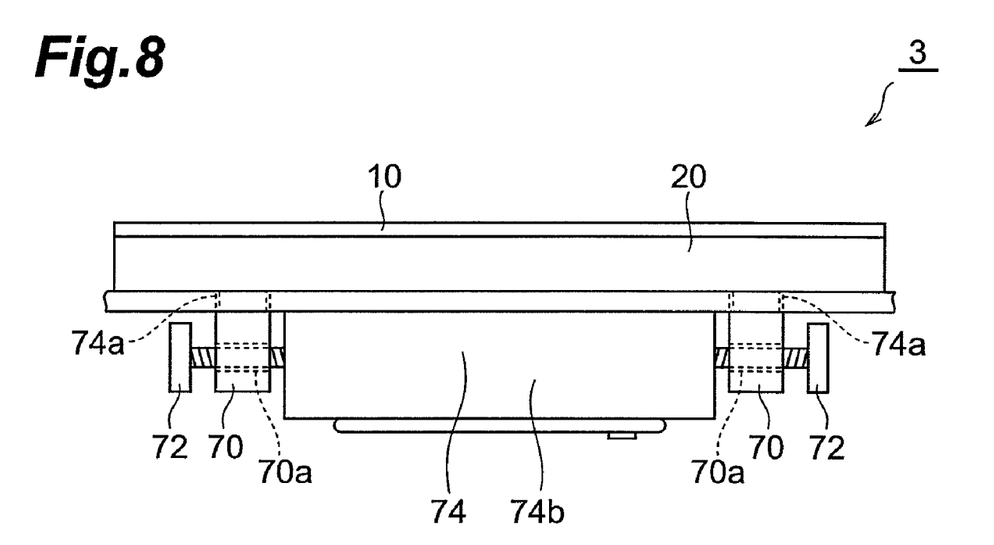
FIG. 8 A side view showing a first modified example of the structure for attachment.

FIG. 8 shows the first modified example of the configuration for attaching a photodetecting unit 3 to a base for attachment 74. In the first modified example, structures for attachment 70 are bar-shaped members each having one end bonded to the rear face of the supporting substrate 20. The leading end of each structure for attachment 70 is formed with a through hole 70a horizontally penetrating through the structure for attachment 70, while the inner face of the through hole 70a is formed with a female thread. The base for attachment 74 is formed with insertion holes 74a penetrating therethrough and corresponding to the respective structures for attachment 70, so that the structures for attachment 70 are inserted through the insertion holes 74a.

A bolt 72 is engaged in a screw thread with the through hole 70a of each structure for attachment 70, so as to penetrate through the structure for attachment 70, whereby the structure for attachment 70 engages in a screw thread with the bolt 72 in thus penetrated part. Since a projection 74b of the base for attachment 74 is arranged between the two structures for attachment 70, the two bolts 72 hold the projection 74b of the base for attachment 74 therebetween when fastened while engaging in a screw thread with the through holes 70a of the structures for attachment 70. This secures the photodetecting units 3 to the base for attachment 74.

The above-mentioned first modified example can accurately arrange the structures for attachment 70 on the rear face of the supporting substrate 20 by fixing the structures for attachment 70 to the fired supporting substrate 20. Therefore, the diameter of the insertion holes 74a in the base for attachment 74 can be made relatively small. This makes it easier for the operator to place the photodetecting unit 3 at a desirable position, thereby improving the attaching operability of the photodetecting unit 3. The first modified example may also be configured such that, instead of abutting the leading ends of two bolts 72 against the base for attachment 74, the base for attachment 74 is formed with a screw hole, and the bolt 72 is fastened into this screw hole. Such a structure can also secure the photodetecting unit 3 to the base for attachment 74.

Figure 9:
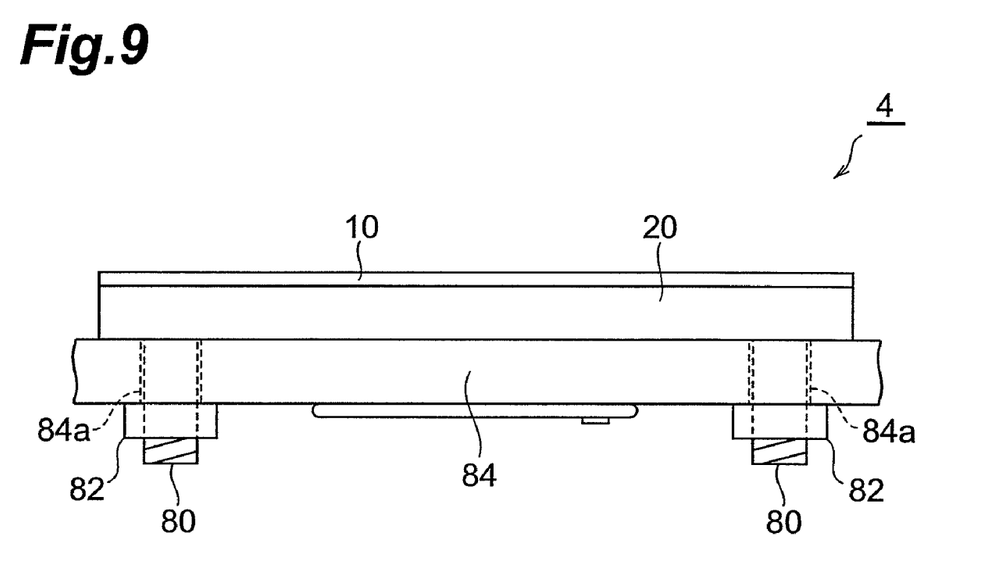
FIG. 9 A side view showing a second modified example of the structure for attachment.

FIG. 9 shows the second modified example of the configuration for attaching a photodetecting unit 4 to a base for attachment 84. In the second modified example, each of two structures for attachment 80 is a bar-shaped member formed with a male thread and has one end bonded to the rear face of the supporting substrate 20. The base for attachment 84 is formed with through holes 84a penetrating therethrough so as to correspond to the structures for attachment 80, which are inserted through the through holes 84a. The leading end of each structure for attachment 80 projects from the through hole 84a for the structure for attachment 80 to the rear side of the base for attachment 84. Nuts 82 are engaged in a screw thread with and fastened onto male threads formed at the projected parts of the structures for attachment 80, whereby the photodetecting unit 4 is secured to the base for attachment 84.

By fixing the structures for attachment 80 to the fired support structure 20, the above-mentioned second modified example can accurately arrange the structures for attachment 80 onto the rear face of the supporting substrate 20. Therefore, the diameter of the through holes 84a in the base for attachment 84 can be made relatively small. This makes it easier for the operator to place the photodetecting unit 4 at a desirable position, thereby improving the attaching operability of the photodetecting unit 4.

Figure 10:
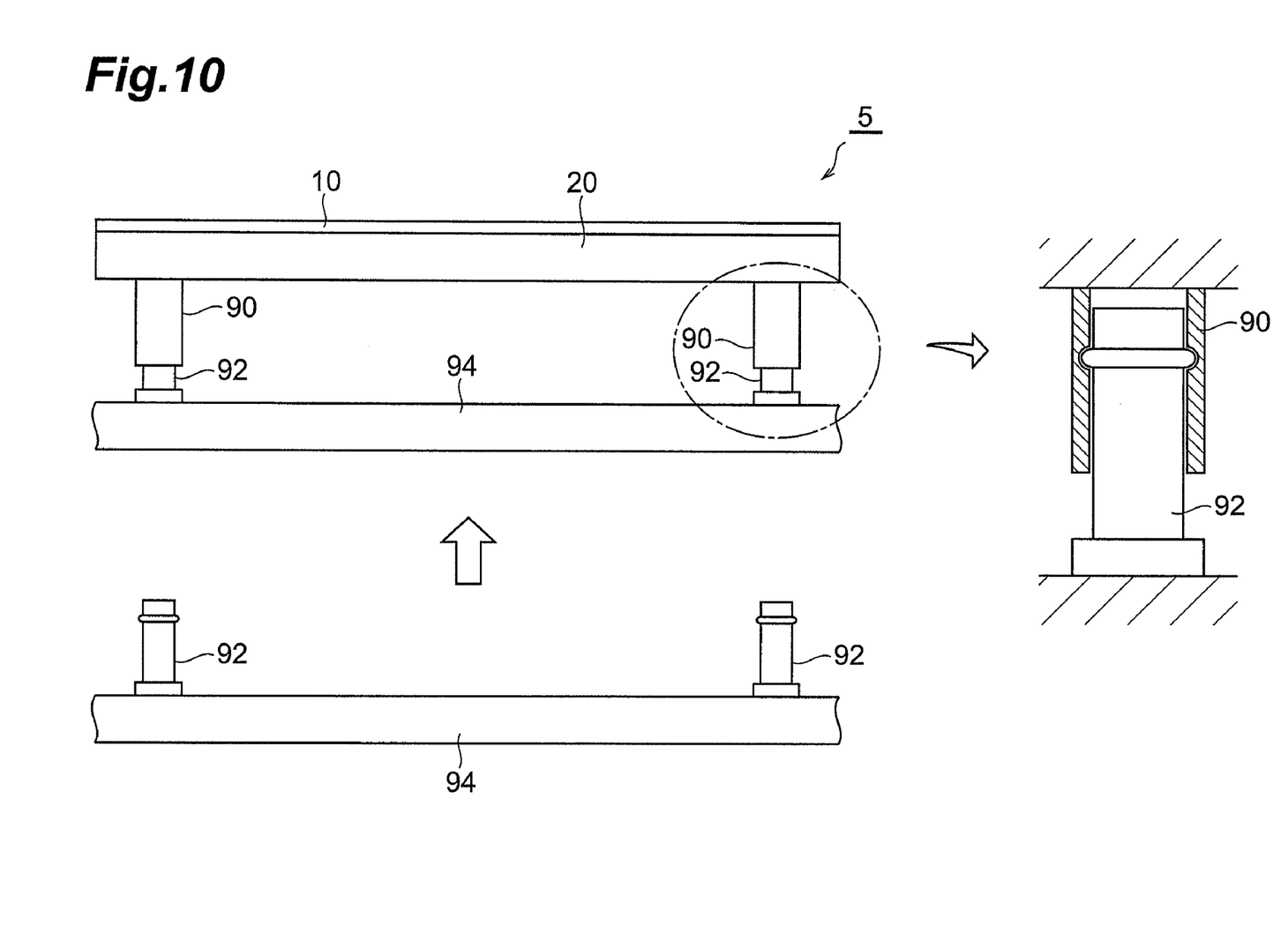
FIG. 10 A side view showing a third modified example of the structure for attachment.

FIG. 10 shows a third modified example of the configuration for attaching a photodetecting unit 5 to an base for attachment 94. In the third modified example, each of two structures for attachment 90 is a member formed with a mating hole and has one end bonded to the rear face of the supporting substrate 20. On the other hand, two mating members 92 adapted to deform elastically in response to external forces are fixed to the base for attachment 94 at positions corresponding to the structures for attachment 90. When the photodetecting unit 5 is pressed against the base for attachment 94, the mating members 92 receive pressures from the respective structures for attachment 90. As a consequence, the mating members 92 fit into the mating holes of the structures for attachment 90 while changing their widths by elastic deformation. Thus, the light-detecting unit 5 is secured to the base for attachment 94.

By securing the structures for attachment 90 to the fired supporting substrate 20, the above-mentioned third modified example can accurately arrange the structures for attachment 90 onto the rear face of the supporting substrate 20. Therefore, when the mating members 92 are accurately arranged on the front face of the base for attachment 94, the photodetecting unit 5 can be arranged at a desirable position if only the mating members 92 are fitted into the mating holes of the structures for attachment 90, which makes it easier for the operator to place the photodetecting unit 5 at a desirable position, thereby improving the attaching operability of the photodetecting unit 5.

The present invention is not limited to the above-mentioned embodiment. For example, though the above-mentioned embodiment explains photodetecting units employed in x-ray tomographic apparatus, the photodetecting units may be those employed in other kinds of apparatus. Though two structures for attachment are fixed to the rear face of the supporting substrate in the above-mentioned embodiment, one or three or more structures for attachment may be fixed thereto.

INDUSTRIAL APPLICABILITY

The present invention can provide a photodetecting unit having a favorable attaching operability.

The invention claimed is:

1. A photodetecting unit comprising:
a semiconductor substrate formed with a photodiode array constructed by arranging a plurality of photodiodes;
a supporting substrate, formed by a sintered body of a ceramic, having a front face arranged with the semiconductor substrate;
a structure for attachment fixed to a rear face of the supporting substrate; and
a tungsten area formed on the rear face of the supporting substrate, wherein the structure for attachment is structurally bonded by silver brazing to the tungsten area.

2. A photodetecting unit according to claim 1, wherein the photodetecting unit comprises at least two structures for attachment, which include said structure for attachment, that are fixed to the rear face of the supporting substrate.

3. A photodetecting unit according to claim 2, wherein the at least two structures for attachment are fixed to the rear face of the supporting substrate each respectively at a location near one of two longitudinal ends thereof, and a connector, for outputting a detected value of photocurrents of the photodiodes to the outside, is fixed to the rear face of the supporting substrate at a region between the two longitudinal ends of the supporting substrate.

4. A photodetecting unit according to claim 3, wherein the connector is situated on the rear face of the supporting substrate at a region that is located outside of a line passing through the two structures for attachment.

5. A photodetecting unit according to claim 1, wherein the structure for attachment is structurally configured such as to be able to threadably engage with a bolt.

6. A photodetecting unit according to claim 1, further comprising a bolt that penetrates through the structure for attachment and wherein the bolt engages in a screw thread included within the structure for attachment.

7. A photodetecting unit according to claim 1, wherein the structure for attachment is structurally configured such as to be able to engage in a screw thread with a nut.

8. A photodetecting unit according to claim 1, further comprising a mating member that mates with the structure for attachment.

9. A photodetecting unit according to claim 1, wherein the silver brazing surrounds and contacts a side face of the structure for attachment on the tungsten area.

10. A photodetecting unit comprising:
a semiconductor substrate formed with a photodiode array constructed by arranging a plurality of photodiodes;
a supporting substrate, formed by a sintered body of a ceramic, having a front face arranged with the semiconductor substrate; and
a structure for attachment fixed to a rear face of the supporting substrate,
wherein one end face of the structure for attachment is structurally bonded by silver brazing to the rear face of the supporting substrate.

11. A photodetecting unit according to claim 10, wherein the photodetecting unit comprises at least two structures for attachment, which include said structure for attachment, that are fixed to the rear face of the supporting substrate.

12. A photodetecting unit according to claim 11, wherein the at least two structures for attachment are fixed to the rear face of the supporting substrate each respectively at a location near one of two longitudinal ends thereof, and a connector, for outputting a detected value of photocurrents of the photodiodes to the outside, is fixed to the rear face of the supporting substrate at a region between the two longitudinal ends of the supporting substrate.

13. A photodetecting unit according to claim 12, wherein the connector is situated on the rear face of the supporting substrate at a region that is located outside of a line passing through the two structures for attachment.

14. A photodetecting unit according to claim 10, wherein the structure for attachment is structurally configured such as to be able to threadably engage with a bolt.

15. A photodetecting unit according to claim 10, further comprising a bolt that penetrates through the structure for attachment and wherein the bolt engages in a screw thread included within the structure for attachment.

16. A photodetecting unit according to claim 10, wherein the structure for attachment is structurally configured such as to be able to engage in a screw thread with a nut.

17. A photodetecting unit according to claim 10, further comprising a mating member that mates with the structure for attachment.

18. A photodetecting unit comprising:
a semiconductor substrate formed with a photodiode array constructed by arranging a plurality of photodiodes;
a supporting substrate, formed by a sintered body of a ceramic, having a front face arranged with the semiconductor substrate; and
a structure for attachment fixed to a rear face of the supporting substrate,
wherein the structure for attachment includes a screw hole or a mating hole, and has one end face that is structurally bonded to the rear face of the supporting substrate.

19. A photodetecting unit according to claim 18, wherein the photodetecting unit comprises at least two structures for attachment, which include said structure for attachment, that are fixed to the rear face of the supporting substrate.

20. A photodetecting unit according to claim 19, wherein the at least two structures for attachment are fixed to the rear face of the supporting substrate each respectively at a location near one of two longitudinal ends thereof, and a connector, for outputting a detected value of photocurrents of the photodiodes to the outside, is fixed to the rear face of the supporting substrate at a region between the two longitudinal ends of the supporting substrate.

21. A photodetecting unit according to claim 20, wherein the connector is situated on the rear face of the supporting substrate at a region that is located outside of a line passing through the two structures for attachment.

22. A photodetecting unit according to claim 18, wherein the structure for attachment is structurally configured such as to be able to threadably engage with a bolt.

23. A photodetecting unit according to claim 18, further comprising a bolt that penetrates through the structure for attachment and wherein the bolt engages in a screw thread included within the structure for attachment.

24. A photodetecting unit according to claim 18, wherein the structure for attachment is structurally configured such as to be able to engage in a screw thread with a nut.

25. A photodetecting unit according to claim 18, further comprising a mating member that mates with the structure for attachment.

26. A photodetecting apparatus comprising:
a photodetecting unit having a semiconductor substrate formed with a photodiode array constructed by arranging a plurality of photodiodes; a supporting substrate formed b a sintered body of a ceramic, having a front face arranged with the semiconductor substrate; and a structure for attachment fixed to a rear face of the supporting substrate; and;
a base for attachment having the photodetecting unit attached thereto through the structure for attachment,
wherein one end face of the structure for attachment is structurally bonded by silver brazing to the rear face of the supporting substrate.

27. A photodetecting apparatus according to claim 26, further comprising a plurality of photodetecting units attached to the base for attachment.

28. A photodetecting apparatus comprising:
a photodetecting unit having a semiconductor substrate formed with a photodiode array constructed by arranging a plurality of photodiodes; a supporting substrate, formed by a sintered body of a ceramic, having a front face arranged with the semiconductor substrate; and a structure for attachment fixed to a rear face of the supporting substrate;
a base for attachment having the photodetecting unit attached thereto through the structure for attachment; and
a tungsten area formed on the rear face of the supporting substrate, wherein the structure for attachment is structurally bonded by silver brazing to the tungsten area.

29. A photodetecting apparatus according to claim 28, further comprising a plurality of photodetecting units attached to the base for attachment.

* * * * *